US010191046B2

(12) United States Patent
Paek et al.

(10) Patent No.: US 10,191,046 B2
(45) Date of Patent: Jan. 29, 2019

(54) IMMUNOBIOSENSOR AND SENSOR SYSTEM INCLUDING THE SAME

(71) Applicants: Se-Hwan Paek, Seoul (KR); KOREA UNIVERSITY RESEARCH AND BUSINESS FOUNDATION, Seoul (KR)

(72) Inventors: Se-Hwan Paek, Seoul (KR); Ji-Na Park, Seoul (KR); Sung-Ho Paek, Seoul (KR)

(73) Assignees: Se-Hwan Paek, Seoul (KR); KOREA UNIVERSITY RESEARCH AND BUSINESS FOUNDATION, Seoul (KR)

(*) Notice: Subject to any disclaimer, the term of this patent is extended or adjusted under 35 U.S.C. 154(b) by 0 days.

(21) Appl. No.: 15/603,212

(22) Filed: May 23, 2017

(65) Prior Publication Data
US 2017/0336405 A1 Nov. 23, 2017

(30) Foreign Application Priority Data

May 23, 2016 (KR) .................. 10-2016-0062585
Apr. 26, 2017 (KR) .................. 10-2017-0053553

(51) Int. Cl.
G01N 33/558 (2006.01)
B01L 3/00 (2006.01)
(Continued)

(52) U.S. Cl.
CPC .......... *G01N 33/558* (2013.01); *B01L 3/5023* (2013.01); *G01N 21/78* (2013.01);
(Continued)

(58) Field of Classification Search
CPC .......... G01N 33/558; G01N 33/54366; G01N 33/54306; G01N 21/78; B01L 3/5023
See application file for complete search history.

(56) References Cited

U.S. PATENT DOCUMENTS 7,300,802 B2* 11/2007 Paek .................. C12Q 1/001
204/403.01
7,998,753 B2* 8/2011 Chiku .................. G01N 33/558
435/7.1
(Continued)

FOREIGN PATENT DOCUMENTS

| KR | 1997-0010882 | 3/1997 | ............. H05K 13/04 |
| KR | 1997-0010882 | 7/1997 | ............. B23K 9/18 |
| KR | 10-1998-074883 | 11/1998 | |

OTHER PUBLICATIONS

Bhargava et al., Gold Nanoparticle Formation during Bromoaurate Reduction by Amino Acids, *Langmuir* 2005, vol. 21, pp. 5949-5946.

*Primary Examiner* — Melanie Brown
(74) *Attorney, Agent, or Firm* — Harness, Dickey & Pierce, P.L.C.

(57) ABSTRACT

An immunobiosensor is disclosed. The immunobiosensor is based on a membrane lateral flow immuno-chromatographic assay (LF-ICA). The immunobiosensor includes: a metal binding protein 10 whose conformation changes upon reaction with a metal ion 1 in a sample; a sensing antibody 20 reacting with the conformationally changed metal binding protein 10 as an antigen; a signal substance 30 conjugated with the metal binding protein 10 or the sensing antibody 20 to form a signal conjugate 30a or 30b; a signal generator 40 reacting with the signal conjugate 30a or 30b to generate a reaction signal; and a reaction strip 50 in the form of a porous membrane adapted to move the sample and where the antigen-antibody reaction occurs and the reaction signal is generated. Also disclosed is a sensor system including the immunobiosensor.

14 Claims, 10 Drawing Sheets

(51) Int. Cl.
*G01N 21/78* (2006.01)
*G01N 21/84* (2006.01)
*G01N 21/77* (2006.01)

(52) U.S. Cl.
CPC .. *G01N 21/8483* (2013.01); *B01L 2300/0654* (2013.01); *B01L 2300/0825* (2013.01); *G01N 2021/7759* (2013.01); *G01N 2021/7786* (2013.01); *G01N 2333/4727* (2013.01)

(56) References Cited

U.S. PATENT DOCUMENTS

| | | | | |
|---|---|---|---|---|
| 2006/0024722 | A1* | 2/2006 | Fischer-Colbrie | B82Y 30/00 435/6.14 |
| 2006/0222567 | A1* | 10/2006 | Kloepfer | G01N 21/78 422/68.1 |
| 2007/0134813 | A1* | 6/2007 | Boga | G01N 33/558 436/518 |
| 2007/0141055 | A1* | 6/2007 | Kajander | G01N 33/57407 424/145.1 |
| 2010/0086930 | A1* | 4/2010 | Soukka | G01N 33/542 435/6.16 |
| 2013/0029322 | A1* | 1/2013 | Jansen-Durr | C07K 16/084 435/5 |
| 2014/0087367 | A1* | 3/2014 | Wada | G01N 33/585 435/5 |
| 2014/0342376 | A1* | 11/2014 | Caussette | G01N 33/558 435/7.32 |
| 2017/0291980 | A1* | 10/2017 | Cain | C08G 8/22 |

* cited by examiner

Determination of the equilibrium binding constant between Complex 1 and the specific antibody.

Comparison of the dose-response curve for the $Ca^{2+}$ immunoassay estimated based on mathematic modeling with that obtained experimentally.

Effect of Ca²⁺ dose in the same sample on performance of the immuno-chromatographic assay using the conventional (A) or two-dimensional (2D) format (B).

Smartphone-based detection system for the color signal produced from the sensor cartridge.

IMMUNOBIOSENSOR AND SENSOR SYSTEM INCLUDING THE SAME

CROSS-REFERENCE TO RELATED APPLICATIONS

This application claims the benefit and priority of Korean Patent Application No. 10-2017-0053553 filed on Apr. 26, 2017 and Korean Patent Application No. 10-2016-0062585 filed on May 23, 2016. The entire disclosure of the above application is incorporated herein by references.

FIELD

The present invention relates to an immunobiosensor and a sensor system including the same. More specifically, the present invention relates to a novel substance (e.g., a specific antibody) that rapidly recognizes a conformational change of a calcium binding protein (CBP) caused by selective binding of polyvalent metal ions ($Ca^{2+}$, $Fe^{2+}$, $Fe^{3+}$, $Zn^{2+}$, $Mn^{2+}$, $Mg^{2+}$, $Cu^{2+}$, etc.) to the calcium binding protein, a novel immunobiosensor for rapid metal ion immunoassay based on the antigen-antibody reaction that can measure metal ions in various analytical applications, including medical diagnosis, animal diagnosis, and food inspection where point-of-care-testing is needed, and a sensor system including the immunobiosensor

BACKGROUND

Biosensors are devices that sense analytes of interest using biometric materials and convert the results into physicochemical signals. Useful biosensors should be selective for particular substances, sensitive to small amounts of analytes, able to respond in a short time, and inexpensive. These requirements determine the performance of biosensors and can increase the competitiveness of biosensors in the market. Many challenges and fierce competition are underway around the world to overcome the functional limitations of existing biosensors while meeting the above requirements. The medical field accounts for about half of the entire biosensor market. Portable, compact, and simple biosensors are emerging in the market that can be used wherever and whenever necessary.

Due to excellent characteristics of biosensors over conventional analyzers, efforts have been dedicated to developing efficient biosensors capable of replacing time-, labor-, and cost-consuming conventional testing methods. Various types of biosensor developed hitherto have been used in various industrial applications, such as medical, environmental, military, and automotive applications. Particularly, the medical diagnostic field is the biggest market of biosensors. Most biosensors have been developed to analyze low-molecular-weight substances, such as internal metabolites (e.g., saccharides), using enzymes as recognition elements and analyze structurally complex substances, such as hormones, proteins, and cells, using specific recognition elements, such as antibodies. Biosensors are of increasing interest in food inspection and safety applications. Under these circumstances, there has been much research aimed at developing biosensors. Biosensors are useful in analyzing not only food constituents, such as carbohydrates, proteins, and fats, but also low-abundant ingredients, such as cholesterol, alcohols, and vitamins. Furthermore, biosensors have been considered promising sensors for detecting harmful substances derived from foods. Biosensors can detect chemicals, such as heavy metals, antibiotics, and agrochemical residues, as well as biological substances, such as microbes.

Ion-selective electrodes (ISEs) are mainly used to detect the presence of polyvalent metal ions ($Ca^{2+}$, $Fe^{2+}$, $Fe^{3+}$, $Zn^{2+}$, $Mn^{2+}$, $Mg^{2+}$, $Cu^{2+}$, etc.) in low-molecular-weight substances. For example, Korean Patent Publication No. 1997-0010882 A discloses an ion-selective electrode including an electrode and a conjugate membrane applied to the electrode wherein a particular metal ion can be selectively attached to the conjugate membrane. However, such conventional ion measurement techniques suffer from the occurrence of false positives and increased measurement variations, leading to poor analytical performance, in the case of analyte samples composed of very complex matrices, such as blood samples. Thus, biosensors using biometric materials need to be developed.

Calcium is the fifth most abundant element in the body and is present in an amount of about 1000 g in the adult body. Calcium is an essential nutrient that is available only through food intake. Of the calcium in the adult body, 99% is distributed in bones and teeth, and the rest is present in blood and soft tissues such as cartilage and muscle fibers. Blood calcium exists in various forms: combined with plasma proteins (40%), interacted in complex manner with anions (e.g., carbonic acid, lactic acid, and fluorophoreic acid; 10%), or liberated as free $Ca^{2+}$ (50%). The free calcium level is about 1.25 mmol/L. Among the different forms of blood calcium, the balance of which is normally maintained, the free ionic portion is physiologically activated only during illness. Blood calcium ion plays a crucial role in blood coagulation and acts as a cofactor for diverse enzymes. Calcium ion is involved in physiological functions such as muscular contraction, neurotransmission, hormone secretion, and intracellular metabolism. Plasma calcium ion level in healthy humans is about 1.1-1.3 mmol/L. Patients whose calcium ion level is ≥1.3 mmol/L are diagnosed as having hypercalcemia and patients whose calcium ion level is ≤1.15 mmol/L are diagnosed as having hypocalcemia. A sudden change in blood calcium ion level adversely affects the body and is a life-threatening signal in severe cases.

A change in blood calcium ion level needs to be monitored and the importance of calcium-containing food intake is being emphasized, leading to the development of various methods for calcium concentration measurement. Current representative methods for the measurement of calcium concentration include chemical, atomic absorption spectroscopy, and chromophore-based spectrophotometry methods, in addition to methods based on the use of ion-selective electrodes (Ms). The most traditional chemical and atomic absorption spectroscopy methods have high accuracy but are disadvantageous in that pretreatment procedures and expensive instruments are required. Electrochemical methods using ion-selective electrodes and chromophore-based spectrophotometry methods have received attention due to their relative simplicity. However, the electrochemical methods have large measurement variations depending on sample composition and lack reproducibility. Another disadvantage of the electrochemical methods is that reagents are difficult to store. Chromophore-based spectrophotometry methods are less selective due to cross-reactivities with other ions.

Furthermore, since the measurement of blood ionic calcium level is greatly affected by blood pH and other environmental conditions, direct measurement after blood collection is most preferred. However, it is difficult to store blood samples isolated from individual patients in large hospitals in view of current medical systems. Further, on-site diagnostic equipment based on ion-selective measurement of ionic calcium is unsuitable for reagent storage and is expensive. For these reasons, large hospitals employ chromophore-based spectrophotometry methods to measure the calcium levels of general patients other than newborns and patients in the intensive care unit. Chromophore-based spectrophotometry methods enable blood storage and can be performed at reduced cost in the central laboratory. Blood calcium levels are calculated from the measured total calcium levels through various algorisms and the calculated values are used for medical diagnosis. As explained above, however, the compensation algorisms are always exposed to problems and limitations and do not perfectly reflect exact calcium ion levels of individual patients.

Current medical diagnostic situations associated with the measurement of polyvalent metal ions ($Ca^{2+}$, $Fe^{2+}$, $Fe^{3+}$, $Zn^{2+}$, $Mn^{2+}$, $Mg^{2+}$, $Cu^{2+}$, etc.) similarly apply to veterinary diagnosis. Particularly, there is an increasing need to measure polyvalent metal ions in the field of food inspection but satisfactory alternatives are not yet available. Since ingredients present in most foods affect human health when ingested or otherwise taken into the body, it is necessary to quantitatively analyze food constituents using various assay techniques. Calcium ion is a typical example of polyvalent metal ions in food ingredients that need to be quantitatively analyzed. Calcium is the most abundant mineral in the body despite its relatively small amount circulating in blood. As explained above, blood calcium ions play a crucial role in regulating and controlling intracellular and extracellular physiological processes. The incidence of disease can be predicted depending on blood calcium ion level. Blood calcium ion level is even involved in the prevention of some cancers or osteoporosis. The elderly are at risk of calcium deficiency. In an effort to reduce this risk, calcium should be supplied through food intake. Currently, the consumption of calcium-containing foods is steadily on the rise.

The above calcium quantification methods can be applied to food samples. However, most of the methods require sample pretreatment, making it difficult to quickly inspect foods or automate periodic analysis processes during food production or management. Particular minerals in food are quantified by chemical methods or atomic absorption spectroscopy methods for quantitative analysis of polyvalent metal ions ($Ca^{2+}$, $Fe^{2+}$, $Fe^{3+}$, $Zn^{2+}$, $Mn^{2+}$, $Mg^{2+}$, $Cu^{2+}$, etc.) after sample pretreatment for metal ion chelation and additional processing for measuring chelated conjugates. In contrast, ion selective electrodes (ISEs) have attracted much attention because of their potential to reduce the number of analysis processes and relative low price. However, currently commercially available ISEs have the problems of low analytical accuracy and poor stability when used to analyze complex samples, such as blood and food samples.

SUMMARY

The present invention has been made in an effort to solve the problems of the prior art, and one object of the present invention is to provide an immunobiosensor using an antibody as a new substance that rapidly recognizes a conformational change of a metal binding protein caused upon binding of a metal ion to the metal binding protein and specifically binds to and reacts with the metal binding protein, enabling quantitative analysis of the metal ion based on the antigen-antibody reaction. Another object of the present invention is to provide a sensor system including the immunobiosensor.

An immunobiosensor of the present invention is based on a membrane lateral flow immuno-chromatographic assay (LF-ICA) and includes: a metal binding protein whose conformation changes upon reaction with a metal ion in a sample; a sensing antibody reacting with the conformationally changed metal binding protein as an antigen; a signal substance conjugated with the metal binding protein or the sensing antibody to form a signal conjugate; a signal generator reacting with the signal conjugate to generate a reaction signal; and a reaction strip in the form of a porous membrane adapted to move the sample and where the antigen-antibody reaction occurs and the reaction signal is generated.

The reaction strip includes a sample addition pad absorbing the sample and a signal generation pad connected to the sample addition pad in the lengthwise direction and immobilized with the metal binding protein or the sensing antibody to generate the reaction signal.

The immunobiosensor of the present invention further includes a conjugate supply pad connecting the sample addition pad to the signal generation pad and supplying the signal conjugate to the signal generation pad. The reaction strip is constructed such that one end of the conjugate supply pad is arranged on one end of the signal generation pad and one end of the sample addition pad is arranged on the other end of the conjugate supply pad, and the immunobiosensor further includes a sample absorption pad arranged on the other end of the signal generation pad to absorb the sample having passed through the signal generation pad.

The signal conjugate is dried into a solid and is arranged on the conjugate supply pad.

The sensing antibody is immobilized on the signal generation pad and a solution of the metal binding protein is absorbed into the sample addition pad or is arranged in the sample addition pad and is dissolved by the sample.

The metal binding protein is immobilized on the signal generation pad and a solution of the sensing antibody is absorbed into the sample addition pad or is arranged in the sample addition pad and is dissolved by the sample.

The signal generator is supplied to the signal generation pad in the widthwise direction of the reaction strip.

The reaction signal is a fluorescence, color, luminescence, electrochemical, thermal or magnetic signal.

The metal ion includes at least one metal ion selected from the group consisting of $Ca^{2+}$, $Fe^{2+}$, $Fe^{3+}$, $Zn^{2+}$, $Mn^{2+}$, $Mg^{2+}$, and $Cu^{2+}$.

The metal ion is a calcium ion, the metal binding protein is a calcium binding protein, the signal substance is biotin, the signal generator is colloidal gold conjugated with streptavidin, and the reaction signal is a color signal generated from the linkage between the biotin and the streptavidin.

The calcium binding protein includes at least one protein selected from the group consisting of glucose-galactose binding proteins, calmodulin, calcium binding enzymes, and genetically substituted proteins.

The sensing antibody includes at least one antibody selected from the group consisting of monoclonal antibodies, polyclonal antibodies, phage display antibodies, and gene recombinant antibodies.

The immunobiosensor of the present invention further includes an accommodation space in which the reaction strip is arranged and a cartridge including a sample inlet through which the sample is introduced into the sample addition pad and a detection window through which signal generation pad is exposed.

A sensor system of the present invention includes: the immunobiosensor; a smart device including a camera capable of capturing a color signal as the reaction signal generated in the signal generation pad of the immunobiosensor as an image; and a holder having a slot into which the immunobiosensor is inserted and adapted to hold the smart device.

The sensor system of the present invention further includes a light source arranged in the smart device holder to emit light.

The captured color signal is converted into digital data by an application on the smart device.

The features and advantages of the present invention will become apparent from the following description with reference to the accompanying drawings.

Prior to the detailed description of the invention, it should be understood that the terms and words used in the specification and claims are construed as having meanings and concepts corresponding to the spirit of the invention in view of the principle that the inventor can define properly the concept of the terms and words in order to describe his/her invention with the best method.

The immunobiosensor of the present invention uses an antibody as a new substance that rapidly recognizes a conformational change of a metal binding protein caused upon binding of a metal ion to the metal binding protein and specifically binds to and reacts with the metal binding protein, enabling quantitative analysis of the metal ion based on the antigen-antibody reaction. The immunobiosensor of the present invention can use an inexpensive chromophore (e.g., colloidal gold), an enzyme, and a fluorophore to generate a signal. In addition, the sensor system of the present invention can use a widespread smartphone to detect the signal, avoiding the need to use an expensive reagent for signal generation or a system for signal measurement.

In addition, the immunobiosensor of the present invention enables immunoassay of metal ions, allowing the measurement of hormones and proteins simultaneously with the analysis of $Ca^{2+}$ under an inexpensive point-of-care testing (POCT) system using a membrane. Thus, the immunobiosensor of the present invention can exactly diagnose various diseases, such as hypercalcemia associated with myeloma and tumors and hypocalcemia associated with renal diseases, parathyroid diseases, osteoporosis, and pancreatitis, in an economical and convenient manner.

Furthermore, the metal ion biosensor technologies of the present invention can be applied to veterinary diagnosis and can be considered alternatives to established technologies in the field of food inspection. Therefore, the immunoassay technologies for polyvalent metal ions according to the present invention are evaluated to be suitable and useful for the paradigm of disease prevention in modern society where people live a long time and an aging population is rapidly increasing.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION

Figure 1:
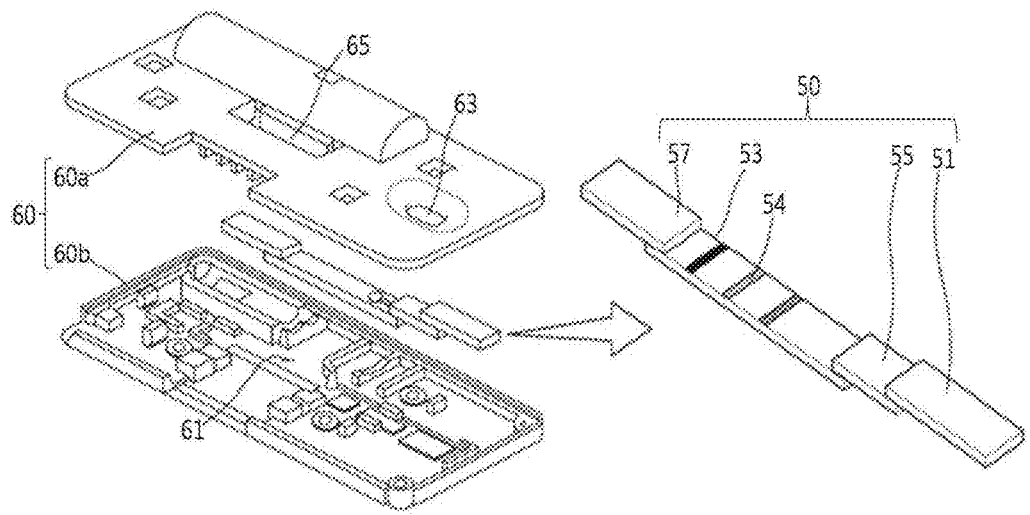
FIG. 1 is an exploded perspective view of an immunobiosensor according to one embodiment of the present invention.

Other objects, advantages, and novel features of the invention will become more apparent from the following detailed description and preferred embodiments with reference to the appended drawings. In the drawings, the same elements are denoted by the same reference numerals even though they are depicted in different drawings. Although the terms as "first" and "second," etc. may be used to describe various elements, these elements should not be limited by above terms. These terms are used only to distinguish one element from another. In the description of the present invention, detailed explanations of related art are omitted when it is deemed that they may unnecessarily obscure the essence of the present invention.

Preferred embodiments of the present invention will now be described in detail with reference to the accompanying drawings.

Figure 2:
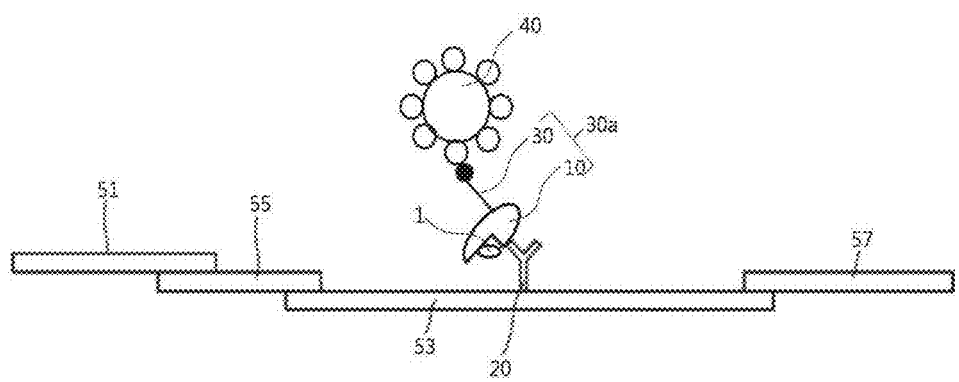
FIGS. 2 and 3 are cross-sectional views of a reaction strip of the immunobiosensor illustrated in FIG. 1.
Figure 3:
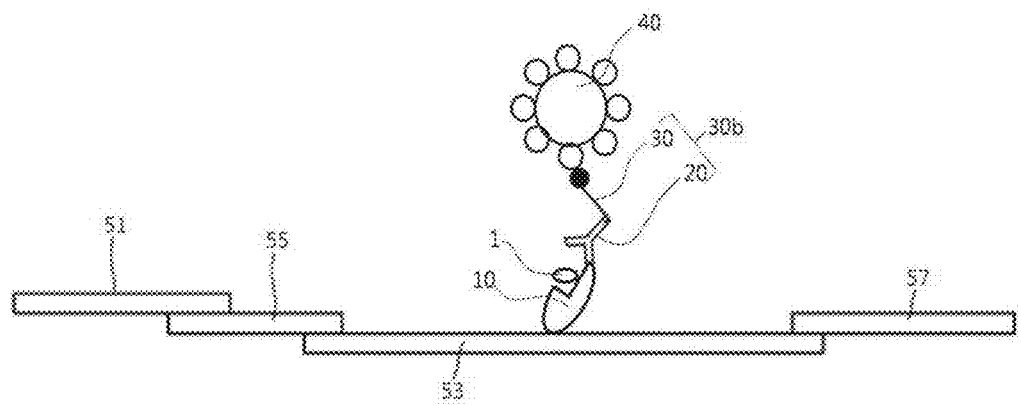
Figure 4:
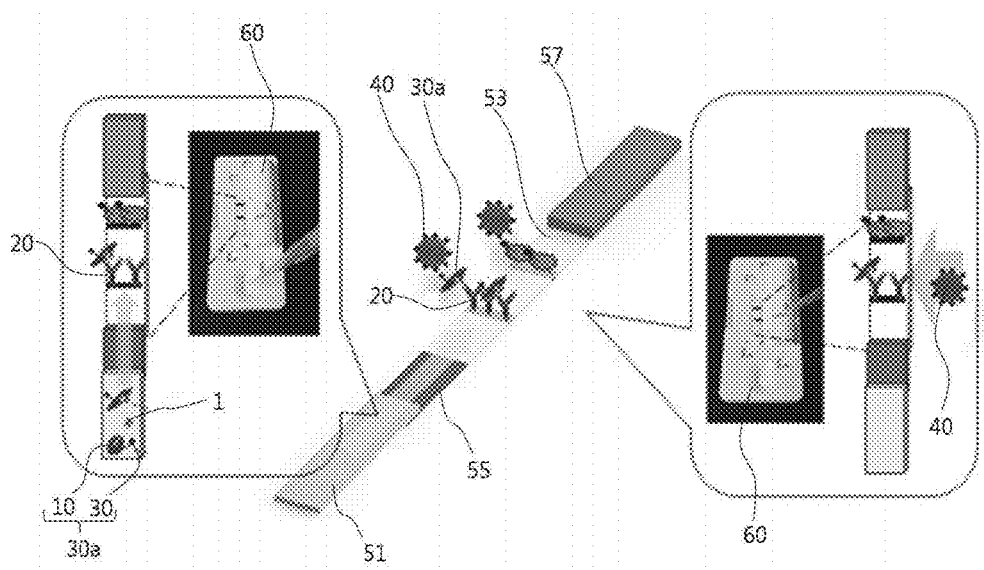
FIG. 4 is a perspective view explaining the principle of operation of an immunobiosensor according to one embodiment of the present invention.

FIG. 1 is an exploded perspective view of an immunobiosensor according to one embodiment of the present invention, FIGS. 2 and 3 are cross-sectional views of a reaction strip of the immunobiosensor illustrated in FIG. 1, and FIG. 4 is a perspective view explaining the principle of operation of an immunobiosensor according to one embodiment of the present invention.

As illustrated in FIGS. 1 to 4, the immunobiosensor of the present invention includes: a metal binding protein 10 whose conformation changes upon reaction with a metal ion 1 in a sample; a sensing antibody 20 reacting with the conformationally changed metal binding protein 10 as an antigen; a signal substance 30 conjugated with the metal binding protein 10 or the sensing antibody 20 to form a signal conjugate 30a or 30b; a signal generator 40 reacting with the signal conjugate 30a or 30b to generate a reaction signal; and a reaction strip 50 in the form of a porous membrane adapted to move the sample and where the antigen-antibody reaction occurs and the reaction signal is generated.

The immunobiosensor of the present invention is based on a membrane lateral flow immuno-chromatographic assay (LF-ICA). LF-ICA is an immunoassay-based point-of-care-testing (POCT) technique. Immuno-chromatography is a testing method that utilizes specific immunoreactivity of antibody against antigen, color developing properties and flowability of colloidal gold, and migration of molecules by the capillary phenomenon in membrane, based on a sandwich immunoassay. LF-ICA has the ability to detect the presence and concentration of an analyte in a sample within a short time even without using expensive equipment. Due to these advantages, LF-ICA is considered the most practical and is widely used in the POCT field.

Specifically, the immunobiosensor of the present invention includes a metal binding protein 10, a sensing antibody 20, a signal substance 30, a signal generator 40, and a reaction strip 50.

The metal binding protein 10 is a protein whose conformation changes upon reaction with a metal ion 1 in a sample. The sample may be body fluid, food, or environmental sample. The metal ion 1 includes at least one metal ion selected from the group consisting of $Ca^{2+}$, $Fe^{2+}$, $Fe^{3+}$, $Zn^{2+}$, $Mn^{2+}$, $Mg^{2+}$, and $Cu^{2+}$ but is not necessarily limited thereto.

The metal binding protein 10 selectively binds to the metal ion 1 and its conformation changes upon binding to the metal ion 1. As the metal binding protein 10, there may be used, for example, a calcium binding protein (CBP). The calcium binding protein calcium binding protein includes at least one protein selected from the group consisting of glucose-galactose binding proteins, calmodulin, calcium binding enzymes, and genetically substituted proteins.

The metal binding protein 10 is mixed with the sample and is then supplied to the reaction strip 50, which will be described below. Alternatively, the metal binding protein 10 may be previously immobilized on the reaction strip 50.

The sensing antibody 20 is an antibody specifically reacting with the metal binding protein 10. The sensing antibody 20 recognizes the conformationally changed metal binding protein 10 as an antigen. The sensing antibody 20 reacts very rapidly and specifically with the metal binding protein 10. In conclusion, only when the metal ion 1 is present in the sample and the conformation of the metal binding protein 10 changes upon reaction with the metal ion 1 does the antigen-antibody reaction occur. The antigen-antibody reaction does not occur in the absence of the metal ion 1 in the sample.

The sensing antibody 20 as a substance recognizing a conformational change of the metal binding protein 10 may include at least one antibody selected from the group consisting of monoclonal antibodies, polyclonal antibodies, phage display antibodies, and gene recombinant antibodies but is not necessarily limited thereto.

The signal substance 30 is a compound that is conjugated with the metal binding protein 10 or the sensing antibody 20. Hereinafter, the resulting conjugate is also referred to as a signal conjugate 30a or 30b. Specifically, the signal conjugate 30a is a conjugate of the metal binding protein 10 and the signal substance 30, and the signal conjugate 30b is a conjugate of the sensing antibody 20 and the signal substance 30. The signal substance 30 may be biotin but is not necessarily limited thereto.

The signal generator 40 is a substance that reacts with the signal conjugate 30a or 30b to generate a reaction signal. The reaction signal may be a fluorescence, color, luminescence, electrochemical, thermal or magnetic signal. The reaction signal is generated only when the signal generator 40 reacts with the signal conjugate 30a or 30b. The signal conjugate 30a or 30b is produced by conjugation of the metal binding protein 10 or the sensing antibody 20 with the signal substance 30. The sensing antibody 20 specifically binds to the metal binding protein 10 having reacted with the metal ion 1. In conclusion, the reaction signal is generated only when the metal ion 1, the metal binding protein 10, the sensing antibody 20, the signal substance 30, and the signal generator 40 participate in their respective reactions. Thus, the presence of the metal ion in the sample can be identified from the reaction signal and the concentration of the metal ion can be calculated by analyzing the intensity of the signal.

The signal generator 40 may be colloidal gold conjugated with streptavidin. At this time, the reaction signal is a color signal generated from the linking rings between the biotin and the streptavidin. The color signal is captured as an image by a suitable tool, such as a camera, its optical density is converted into digital data by a suitable program, and the data is analyzed to calculate the concentration of the metal ion 1. The metal ion 1 is particularly $Ca^{2+}$.

The reaction strip 50 is a member that has a predetermined length and is in the form of a porous membrane through which the sample moves by capillary force. Since the metal ion 1 and the signal conjugate 30a or 30b move along the moving sample, the antigen-antibody reaction occurs and the reaction signal is generated on the reaction strip 50.

Specifically, the reaction strip 50 may include a sample addition pad 51 and a signal generation pad 53.

The sample addition pad 51 is a part of the reaction strip 50 where the externally supplied sample is absorbed. The sample addition pad 51 may be made of a polyester for sample loading. However, the material for the sample addition pad 51 is not necessarily limited to a polyester.

In addition to the sample, the metal binding protein 10 or the sensing antibody 20 may be added to the sample addition pad 51. The metal binding protein 10 or the sensing antibody 20 is introduced in the form of a solution from the outside and is absorbed into the sample addition pad 51. Alternatively, the metal binding protein 10 or the sensing antibody 20 is dried into a solid, is arranged on the sample addition pad 51, dissolved by the sample, and transferred to the subsequent pad. The metal binding protein 10 or the sensing antibody 20 does not need to be added to the sample addition pad 51 and may be added to a conjugate supply pad 55, which will be described below.

The signal generation pad 53 is a part connected to the sample addition pad 51 in the lengthwise direction and has an analyte site 54. The analyte site 54 is a site on the signal generation pad 53 on which the metal binding protein 10 or the sensing antibody 20 is immobilized.

When the sensing antibody 20 is immobilized on the signal generation pad 53 (see FIG. 2), the metal binding protein 10 is conjugated with the signal substance 30 to produce the signal conjugate 30a and the metal ion 1 in the sample binds to the conjugated metal binding protein 10. The conformational changed metal binding protein 10 reacts with the sensing antibody 20 immobilized on the analyte site 54, and thereafter, the externally supplied signal generator 40 reacts with the signal conjugate 30a to generate a reaction signal. In this case, the metal binding protein 10 may be added to the sample addition pad 51 or a conjugate supply pad 55, which will be described below.

Alternatively, the metal binding protein 10 may be immobilized on the signal generation pad 53 (see FIG. 3). In this case, the sensing antibody 20 and the signal substance 30 form the signal conjugate 30b, the metal ion 1 present in the sample binds to the metal binding protein 10, and the sensing antibody 20 reacts with the metal binding protein 10 on the signal generation pad 53. Thereafter, the signal generator 40 is supplied from the outside to generate a reaction signal. Here, the sensing antibody 20 may be added to the sample addition pad 51 or a conjugate supply pad 55, which will be described below.

The reaction strip 50 may further include a conjugate supply pad 55. The conjugate supply pad 55 is a part of the reaction strip 50 that is arranged between the sample addition pad 51 and the signal generation pad 53 to connect the two pads. The conjugate supply pad 55 supplies the signal conjugate 30a or 30b to the signal generation pad 53 when the sample absorbed into the sample addition pad 51 moves in the lengthwise direction (vertical flow).

First, in the case where the metal binding protein 10 and the signal substance 30 form the signal conjugate 30a, as illustrated in FIG. 2, the signal conjugate 30a may be dried into a solid and arranged on the conjugate supply pad 55. Alternatively, only the signal substance 30 may be arranged in the conjugate supply pad 55 and the metal binding protein 10 may be introduced into the conjugate supply pad 55 through the sample addition pad 51. Alternatively, the metal binding protein 10 and the signal substance 30 may be introduced into the conjugate supply pad 55 through the sample addition pad 51. The metal binding protein 10 is conjugated with the signal substance 30 in the conjugate supply pad 55 and the signal conjugate 30a is supplied through the conjugate supply pad 55.

Alternatively, in the case where the sensing antibody 20 and the signal substance 30 form the signal conjugate 30b, as illustrated in FIG. 3, the signal conjugate 30b may be dried into a solid and arranged in the conjugate supply pad 55. Alternatively, only the signal substance 30 may be arranged in the conjugate supply pad 55 and the sensing antibody 20 may be introduced into the conjugate supply pad 55 through the sample addition pad 51. Alternatively, the sensing antibody 20 and the signal substance 30 may be introduced into the conjugate supply pad 55 through the sample addition pad 51. The sensing antibody 20 is conjugated with the signal substance 30 in the conjugate supply pad 55 and the signal conjugate 30b is supplied through the conjugate supply pad 55.

On the other hand, a reaction signal is generated in the signal generation pad 53 of the reaction strip 50. At this time, the signal generator 40 may be supplied to the signal generation pad 53 in the widthwise direction (horizontal flow) of the reaction strip 50. Referring to FIG. 4, when the signal conjugate 30a produced by conjugation of the metal binding protein 10 and the signal substance 30 migrates in the lengthwise direction (vertical flow), the metal binding protein 10 binds to the metal ion 1 and specifically reacts with and is immobilized on the sensing antibody 20 arranged on the signal generation pad 53. At this time, the signal generator 40 is supplied to the signal generation pad 53 from the lateral direction and reacts with the signal conjugate 30a to generate a reaction signal.

Here, the reaction strip 50 may further include a sample absorption pad 57 capable of absorbing the sample having passed through the signal generation pad 53. The sample addition pad 51, the conjugate supply pad 55, the signal generation pad 53, and the sample absorption pad 57 are sequentially arranged in the lengthwise direction such that one end of the conjugate supply pad 55 is arranged on one end of the signal generation pad 53, one end of the sample addition pad 51 is arranged on the other end of the conjugate supply pad 55, and the sample absorption pad 57 is arranged on the other end of the signal generation pad 53. Here, the conjugate supply pad 55 and the sample absorption pad 57 are arranged at both ends of the signal generation pad 53 to form stepped portions. This arrangement enables effective transfer of the signal generator 40 in the widthwise direction of the signal generation pad 53.

The immunobiosensor of the present invention may further include a cartridge in which the reaction strip 50 is accommodated (see FIGS. 1 and 4). The cartridge 60 has an accommodation space 61 in which the reaction strip 50 is accommodated. The cartridge 60 has a sample inlet 63 through which the accommodation space 61 is in communication with the outside and the sample is introduced into the reaction strip 50. The cartridge 60 has a detection window 65 through which the signal generation pad 53 is exposed. The reaction signal on the analyte site 54 can be easily observed from the outside through the detection window 65.

The cartridge 60 consists of an upper plate 60a and a lower plate 60b separately coupled to each other. The reaction strip 50 may be arranged between the upper plate 60a and the lower plate 60b. However, the cartridge 60 may not necessarily consist of the upper plate 60a and the lower plate 60b. For example, the cartridge 60 may be produced in one piece in which the reaction strip 50 is inserted.

Figure 5:
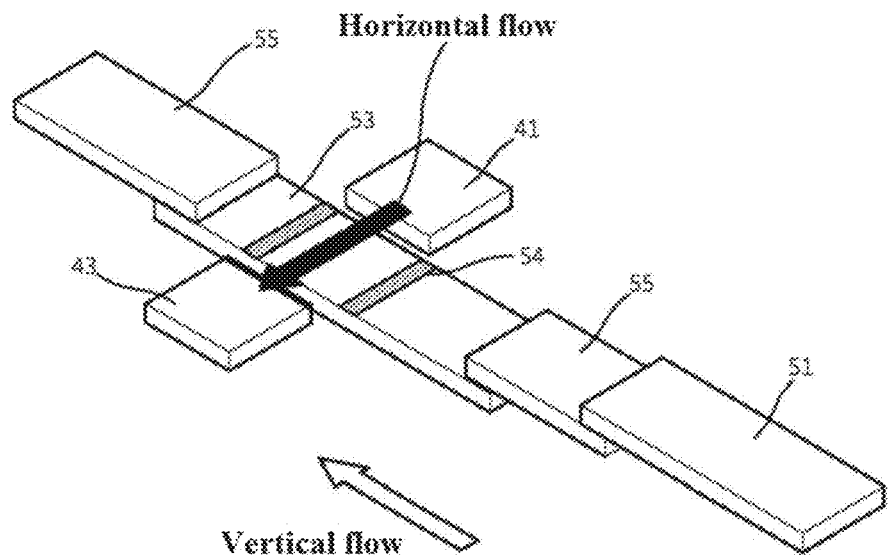
FIG. 5 is a perspective view of an immunobiosensor according to a further embodiment of the present invention.

FIG. 5 is a perspective view of an immunobiosensor according to a further embodiment of the present invention.

As illustrated in FIG. 5, the immunobiosensor according to this embodiment of the present invention may further include a signal generator supply pad 41 and a signal generator absorption pad 43. One of the signal generator supply pad 41 and the signal generator absorption pad 43 is arranged at one side of the signal generation pad 53 and the other one is arranged at the other side of the signal generation pad 53. With this arrangement, the signal generator 40 introduced into the signal generator supply pad 41 is transferred in the widthwise direction of the signal generation pad 53 and is absorbed into the signal generator absorption pad 43.

The metal ion sensed by the immunobiosensor of the present invention can be detected and quantitatively analyzed in situ using a smartphone-based signal detection system on site. The system will be explained below.

Figure 6:
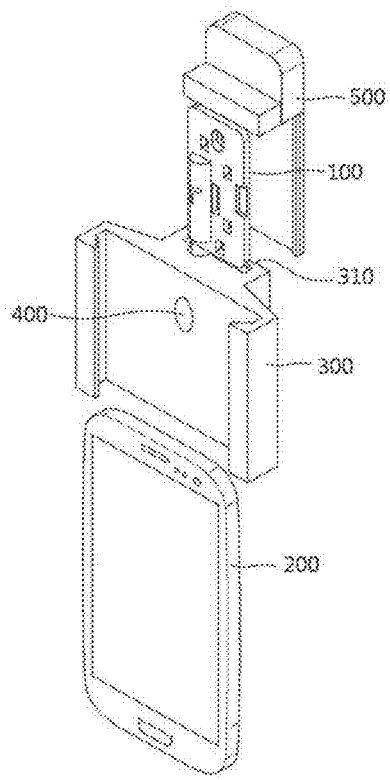
FIG. 6 is an exploded perspective view of a sensor system according to one embodiment of the present invention.

FIG. 6 is an exploded perspective view of a sensor system according to one embodiment of the present invention;

As illustrated in FIG. 6, the sensor system of the present invention includes: the immunobiosensor 100; a smart device 200 including a camera capable of capturing a color signal as the reaction signal generated in the signal generation pad 53 (see FIGS. 2 to 4) of the immunobiosensor 100 as an image; and a holder 300 having a slot 310 into which the immunobiosensor 100 is inserted and adapted to hold the smart device 200.

The immunobiosensor 100 is the same as that described above and its detailed description thereof is thus omitted.

The smart device 200 refers to a device, such as a smartphone, a tablet computer or a notebook computer, whose function is not limited and can be altered or extended to a considerable extent through an application program, such as a mobile application. A camera is installed in the smart device 200. The lens of the camera is arranged to face the analyte site 54 of the signal generation pad 53. With this arrangement, the camera can capture the color signal as an image.

The smart device 200 and the immunobiosensor 100 is held by the smart device holder 300. The smart device holder 300 has a stand holding the smart device 200 and a slot 310 into which the immunobiosensor 100 is inserted. The immunobiosensor 100 inserted into the slot 310 may be fixed by a cover 500.

The sensor system of the present invention may further include a focusing lens 400. The focusing lens 400 is adapted to control the focal distance of the camera. The focusing lens 400 can be arranged between the camera and the analyte site 54 to improve the resolution of the color signal image.

The sensor system of the present invention further includes a light source arranged in the smart device holder 300. The light source may be, for example, an LED lamp. The light source can be automatically turned on when the smart device 200 is held by the stand. The immunobiosensor 100 is inserted into the slot 310 and the camera can capture the color signal generated from the immunobiosensor 100 as an image.

The captured image is converted into digital data, which can be utilized as information for quantitative analysis. The conversion can be accomplished by a suitable application on the smart device 200.

Overall, the immunobiosensor of the present invention uses an antibody as a new substance that rapidly recognizes a conformational change of a metal binding protein caused upon binding of a metal ion to the metal binding protein and specifically binds to and reacts with the metal binding protein, enabling quantitative analysis of the metal ion based on the antigen-antibody reaction. The immunobiosensor of the present invention can use an inexpensive chromophore (e.g., colloidal gold), an enzyme, and a fluorophore to generate a signal. In addition, the sensor system of the present invention can use a widespread smartphone to detect the signal, avoiding the need to use an expensive reagent for signal generation or a system for signal measurement.

In addition, the immunobiosensor of the present invention enables immunoassay of metal ions, allowing the measurement of hormones and proteins simultaneously with the analysis of $Ca^{2+}$ under an inexpensive point-of-care testing (POCT) system using a membrane. Thus, the immunobiosensor of the present invention can exactly diagnose various diseases, such as hypercalcemia associated with myeloma and tumors and hypocalcemia associated with renal diseases, parathyroid diseases, osteoporosis, and pancreatitis, in an economical and convenient manner.

Furthermore, the metal ion biosensor technologies of the present invention can be applied to veterinary diagnosis and can be considered alternatives to established technologies in the field of food inspection. Therefore, the immunoassay technologies for polyvalent metal ions according to the present invention are evaluated to be suitable and useful for the paradigm of disease prevention in modern society where people live a long time and an aging population is rapidly increasing. The present invention will be explained in more detail with reference to the following examples. These examples are merely illustrative and the scope of the present invention is not limited thereto.

Figure 7:
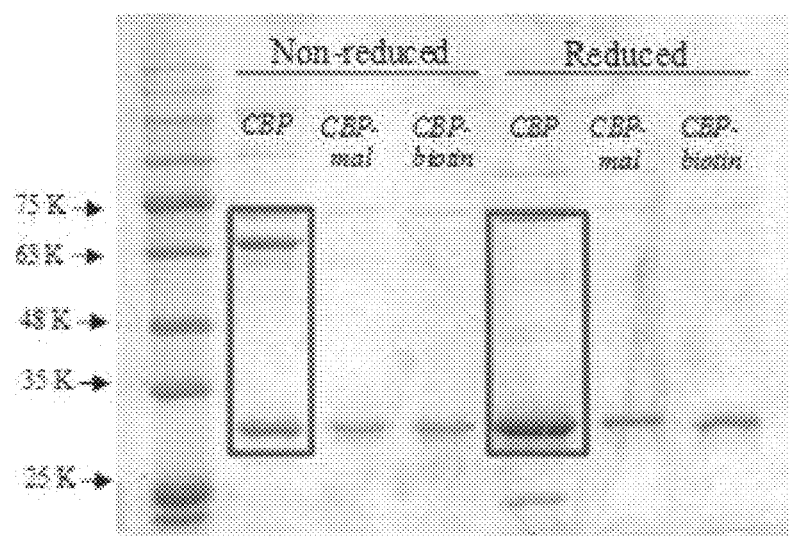
FIG. 7 is an image showing the results of polyacrylamide gel electrophoresis for the molecular size of a calcium binding protein used in the present invention.
Figure 8:
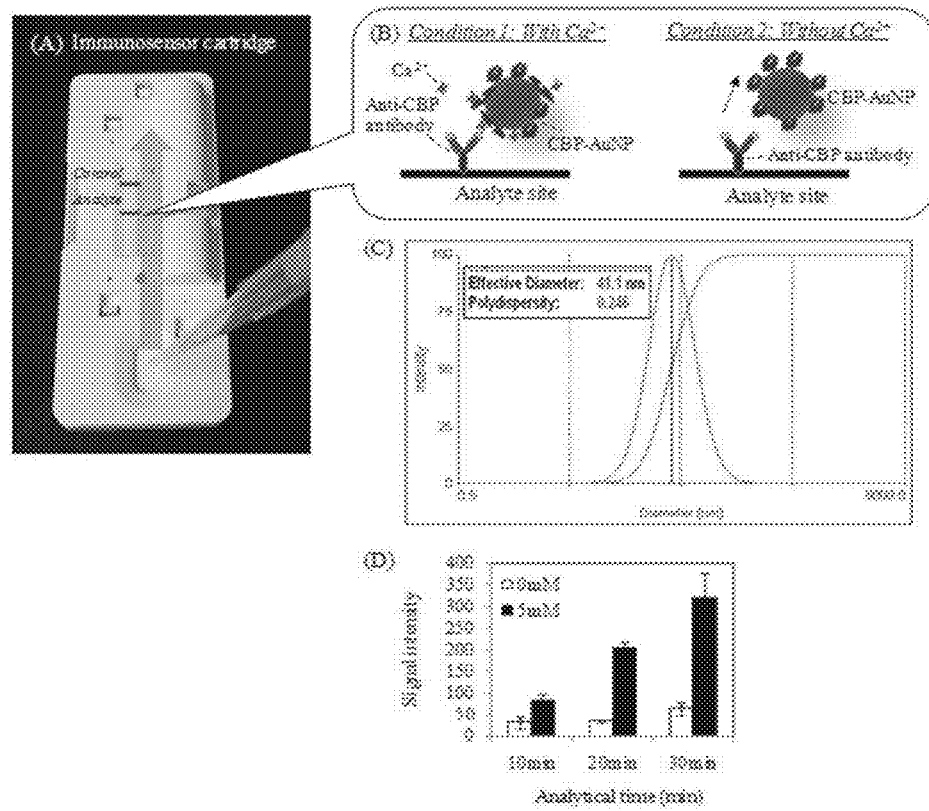
FIG. 8 graphically shows the binding characteristics between a calcium binding protein and $Ca^{2+}$ at equilibrium.
Figure 8:
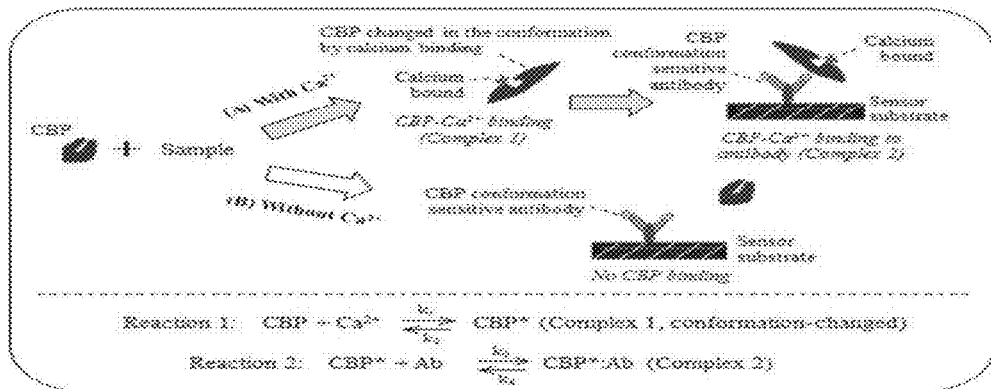
Figure 9:
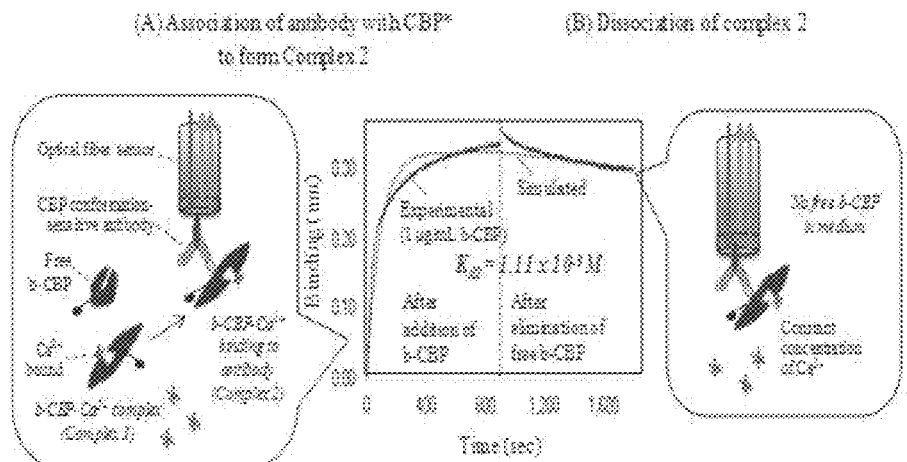
FIG. 9 graphically shows the binding force of an antibody specifically recognizing a conformational change of a calcium binding protein caused when $Ca^{2+}$ binds to the calcium binding protein.

FIG. 7 is an image showing the results of polyacrylamide gel electrophoresis for the molecular size of a calcium binding protein used in the present invention, FIG. 8 graphically shows the binding characteristics between a calcium binding protein and $Ca^{2+}$ at equilibrium, and FIG. 9 graphically shows the binding force of an antibody specifically recognizing a conformational change of a calcium binding protein caused when $Ca^{2+}$ binds to the calcium binding protein.

Figure 10:
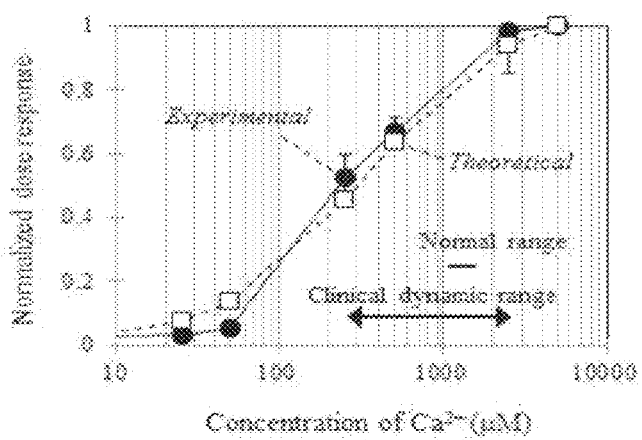
FIG. 10 graphically compares a theoretical standard curve for $Ca^{2+}$ immunoassay calculated based on mathematic modeling with a standard curve obtained experimentally.
Figure 11:
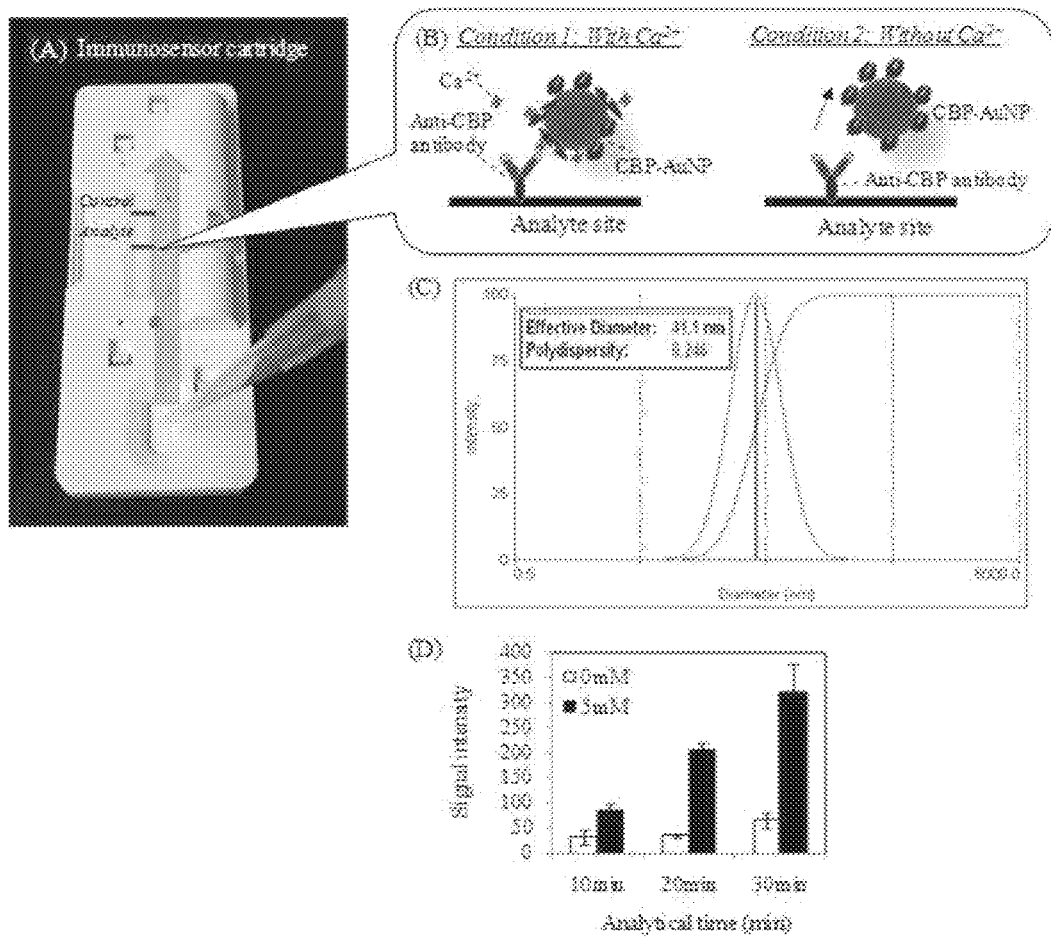
FIG. 11 shows diagrams suggesting the problems encountered in the analysis of $Ca^{2+}$ present in a sample by a conventional immunoassay based on 1-dimensional chromatography using colloidal gold.
Figure 12:
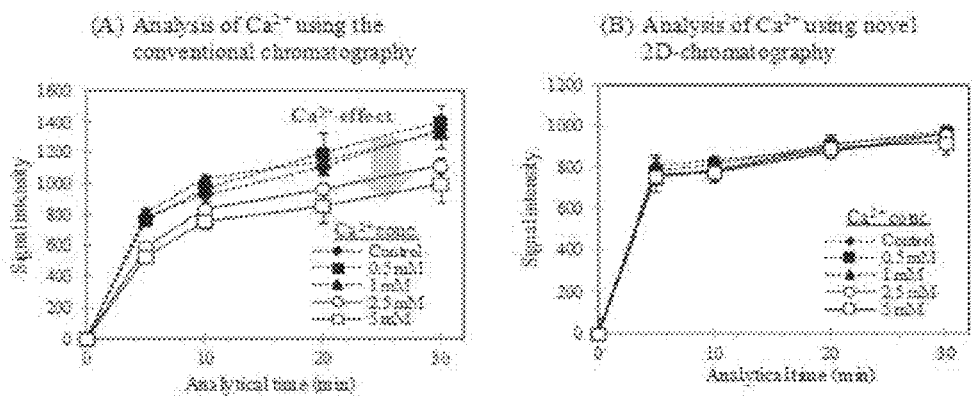
FIG. 12 compares non-specific effects of $Ca^{2+}$ dose by a general immuno-chromatographic assay using colloidal gold, which were measured using conventional and two-dimensional formats.

FIG. 10 graphically compares a theoretical standard curve for $Ca^{2+}$ immunoassay calculated based on mathematic modeling with a standard curve obtained experimentally, FIG. 11 shows diagrams suggesting the problems encountered in the analysis of $Ca^{2+}$ present in a sample by a conventional immunoassay based on 1-dimensional chromatography using colloidal gold, and FIG. 12 compares non-specific effects of $Ca^{2+}$ dose by a general immunochromatographic assay using colloidal gold, which were measured using conventional and two-dimensional formats.

Figure 13:
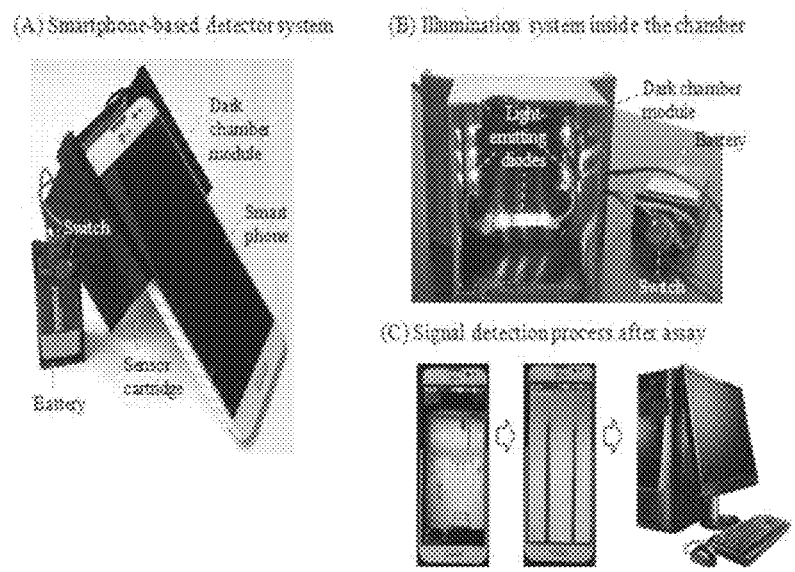
FIG. 13 shows actual images of a sensor system according to one embodiment of the present invention.
Figure 14:
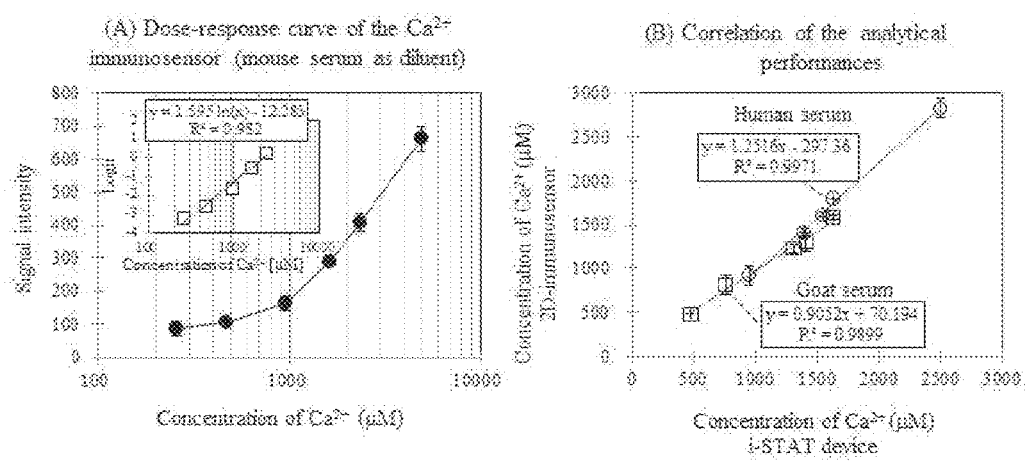
FIG. 14 graphically shows the dynamic range of an immunobiosensor according to one embodiment of the present invention and the analytical correlation with a reference system.
Figure 15:
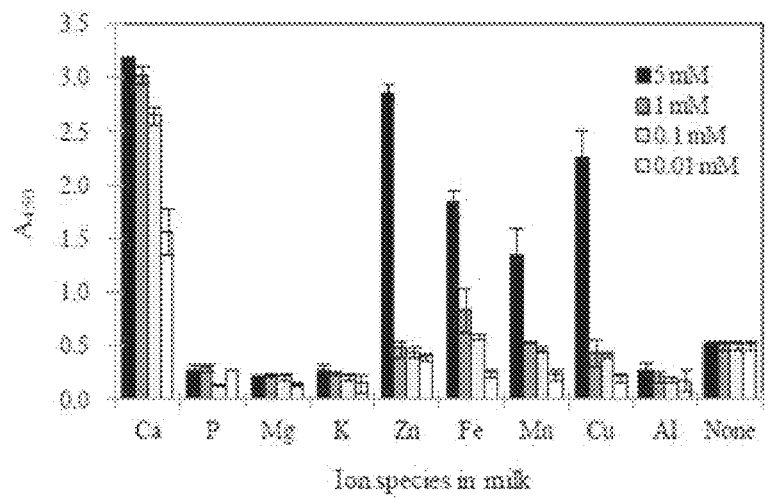
FIG. 15 graphically shows the reactivities with a calcium binding protein for eight different cations contained in human serum and raw cow milk.
Figure 16:
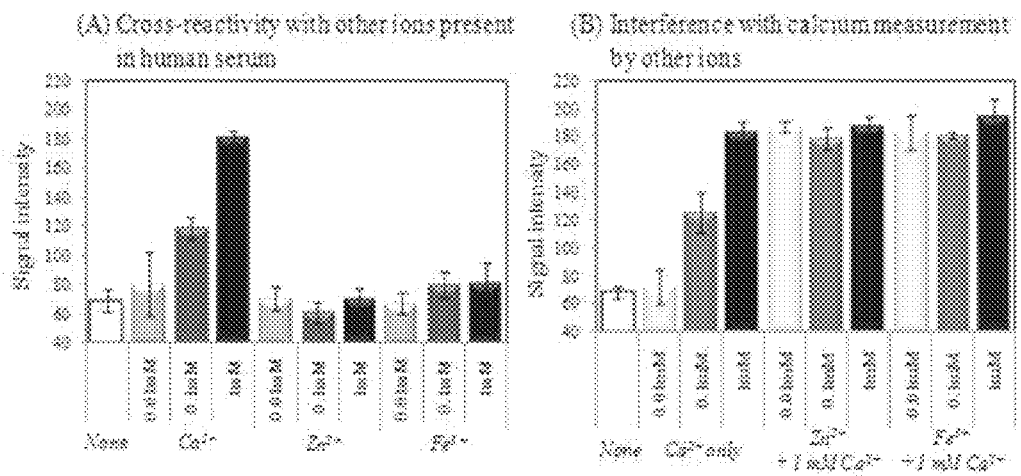
FIG. 16 graphically shows the reactivities of cations with a calcium binding protein and demonstrates the absence of interference with calcium measurement in the actual concentration ranges of the cations in human serum or raw cow milk.

FIG. 13 shows actual images of a sensor system according to one embodiment of the present invention, FIG. 14 graphically shows the dynamic range of an immunobiosensor according to one embodiment of the present invention and the analytical correlation with a reference system, FIG. 15 graphically shows the reactivities with a calcium binding protein for eight different cations contained in human serum and raw cow milk, and FIG. 16 graphically shows the reactivities of cations with a calcium binding protein and demonstrates the absence of interference with calcium measurement in the actual concentration ranges of the cations in human serum or raw cow milk.

Material Preparation

A monoclonal antibody specifically recognizing a conformational change of a calcium binding protein caused by specific binding to $Ca^{2+}$ was directly produced in laboratory. The calcium binding protein used in the present invention was isolated by genetic recombination of the E. coli glucose-galactose binding protein. Sodium chloride, casein (sodium salt form, extracted from milk), 3,3',5,5'-tetramethylbenzidine dihydrochloride (rim), and gold chloride ($HAuCl_4$) were purchased from Sigma (St. Louis, Mo., USA). Calcium chloride and potassium chloride were purchased from Daejung (Siheung, Korea). Ez-Link BMCC-biotin, succinimidyl 4-(N-maleimidomethyl) cyclohexane-1-carboxylate (SMCC), N-succinimidyl 3-(2-pyridyldithio)-propionate (SPDP), dithiothreitol (DTT), maleimide, streptavidin, and horseradish peroxidase were purchased from Thermo Fisher Scientific (Rockford, Ill., USA). Colloidal gold with an average particle size of 41.1 nm was synthesized by the sodium citrate method (Bhargava et al. 2005). Glass fiber membranes (PT-R5) and sample addition pads (GFB-R4) were supplied from MDI (Ambala. Cantt, India). NC membranes (HiFlowPlus HFB 13504) and cellulose membranes (17CHR, chromatography grade) were purchased from Millipore (Billerica, Mass., USA) and Whatman (Maidstone, UK), respectively. Quartz glass cells for spectrophotometers were purchased from Hellma (Miihlheim, Germany). Anti-mouse (AMC) sensor tips of Octet Red were supplied from ForteBio (San Francisco, Calif., USA). All reagents were analytical grade.

Example 1: $Ca^{2+}$ Immunoassay

1) Production of Calcium Binding Protein

A biosensor capable of quantitatively measuring $Ca^{2+}$ was constructed. To this end, a glucose-galactose binding protein (GGBP) present in the cytoplasmic membrane of E. coli, a gram-negative bacterial species, was selected as a calcium binding protein that recognizes $Ca^{2+}$. The calcium binding protein is a genetic recombinant protein that has one $Ca^{2+}$ binding site and whose molecular constituent amino acid sequence Phe16 was substituted with alanine. Since this protein has one cysteine residue in the molecule, the residue is suitable for labeling with a signal. generating substance (e.g., colloidal gold) by covalent bonding of the signal generating substance to a designated sulfhydryl group. The sulfhydryl group is provided by the reduction of the cysteine residue. The sulfhydryl group remaining in one calcium binding protein molecule after labeling is likely to exist as a dimer with the sulthydryl group of another molecule through disulfide bridge formation. In consideration of this, the remaining sulfhydryl group was inactivated by reaction with maleimide or maleimide-derivatized biotin. Electrophoresis of the finally produced calcium binding protein revealed that the molecular weight of the calcium binding protein matched the original value (34 kDa) (see FIG. 7).

2) Determination of Affinity of the Calcium Binding Protein for $Ca^{2+}$

The calcium binding protein contains 5 auto-fluorescent tryptophan residues (Trp127, Trp133, Trp183, Trp 195, and Trp284) in the molecule. The calcium binding protein undergoes a conformational change when bound to $Ca^{2+}$. The conformational change of the calcium binding protein changes the environment around the tryptophan residues and the intensity of the auto-fluorescence. Based on this principle, changes in the auto-fluorescence intensity of the calcium binding protein as a function of $Ca^{2+}$ concentration were measured using a spectrofluorometer (F-7000, Hitachi; Japan) at a maximum absorbance of 336.6 nm (see A of FIG. 8). The measured values were plotted according to the Linear Weaver equation. From the slope, the affinity of the calcium binding protein for $Ca^{2+}$ was determined (equilibrium dissociation constant ($K_{d1}$): $k_2/k_1 = 3.4 \times 10^{-4}$ M; see Reaction 1) (see B of FIG. 8).

3) Production and Characterization of Monoclonal Antibody

The standard hybridoma production process was used to produce a monoclonal antibody that specifically recognizes a conformational change of the calcium binding protein caused by binding to $Ca^{2+}$.

The calcium binding protein (40 μg/mouse) was emulsified with complete Freund's adjuvant (150 μL) diluted two-fold with phosphate-buffered saline (pH 7.4) and was intraperitoneally injected into four 6-week-old old female Balb/c mice to immunize the mice. Thereafter, the animals were further immunized twice with the same immunogen emulsified with incomplete Freund's adjuvant at a two-week interval. A serum sample was collected from each mouse before immunization ("control") and a serum sample was collected from the same mouse 7 days after immunization. The activity of antibody against the serum samples was tested through an enzyme-linked immunosorbent assay (ELISA) on microtiter wells immobilized with the calcium binding protein (see below for details).

Spleen cells harvested from the immunized mice were fused with myeloma cells (sp2/0 Ag14) in accordance with the standard protocol. The fused hybridoma cells were screened in accordance with the HAT selection procedure and the activity of the antibody produced from each cell was tested by ELISA using the immobilized calcium binding protein. Hybridoma clones with various activities were first screened and cultured from the single cell using the limited dilution method.

Antibodies with reactivity against a unique conformational change of the calcium binding protein caused in the presence of $Ca^{2+}$ compared to in the absence of $Ca^{2+}$ were selected from the screened cell clones. To this end, the calcium binding protein (1 μg/mL; 100 μL/well) was diluted with 10 mM Tris buffer (pH 7.4; Tris solution) containing 140 mM NaCl, plated in microwells, and immobilized at 37° C. for 1 h. The wells were washed three times with deionized water and the remaining surface was blocked with a 0.5% casein solution in Tris solution (Tris-Casein). The antibody produced from each cell culture was diluted ten-fold with Tris-Casein solution (Tris-Casein-$CaCl_2$-TW) containing 1 mM $CaCl_2$ and 0.1% Tween20, added to each well, and was allowed to react under the same conditions. Each well was washed with Tris solution containing 1 mM $CaCl_2$ ($CaCl_2$-Tris) and the protein was allowed to react with horseradish peroxidase (HRP)-labeled anti-mouse goat antibody diluted with Tris-Casein-$CaCl_2$-TW solution. The well was again washed with $CaCl_2$-Tris solution and added with HRP enzyme substrate solution (100 vL; containing tetramethyl benzidine). The chromogenic reaction was performed at room temperature for 15 min and was stopped with a 2 M sulfuric acid solution (50 μL). The optical density of the color generated from each well was measured using a microtiter plate reader (Versa Max; Molecular Devices, Sunnyvale, USA) at an absorbance of 450 nm. The same procedure was repeated using a $Ca^{2+}$-free solution in order to confirm the negative reaction of the antibody in the absence of $Ca^{2+}$ in solution.

In order to determine the binding force of the finally selected monoclonal antibody, Octet Red, a label-free sensor system, was used to measure the kinetics of the antibody against the conformational changed calcium binding protein in the presence of $Ca^{2+}$ (see the association reaction (A) and dissociation reaction (B) in FIG. 9). The antibody was immobilized on the surface of the Octet sensor, a solution of the calcium binding protein was added, and association and dissociation reactions were performed with and without $Ca^{2+}$. As a result, the affinity (equilibrium dissociation constant ($K_{d2}$): $k_4/k_3$; see Reaction 2 of FIG. 8) was determined to be $1.11 \times 10^{-9}$ M (see FIG. 9).

4) Mathematic Modeling

For quantitative analysis of $Ca^{2+}$, an analytical solution was obtained through mathematic modeling of the reactions shown in FIG. 8 at equilibrium and a response from an immunoassay system to a change in the concentration of $Ca^{2+}$ was calculated therefrom (see "Biosensors and Bioelectronics", 85, 611-617, 2016). Parameter values necessary for this calculation were experimentally measured and substituted into the mathematic model. The signal of the immunoassay system determined at each $Ca^{2+}$ concentration was calculated as the number of moles of the antibody having reacted with the conformationally changed calcium binding protein and was plotted as a dose-response curve (FIG. 10, Theoretical).

5) Experimental Model

To determine whether the mathematically calculated dose-response curve matched the dose-response curve obtained experimentally, an actual $Ca^{2+}$ immunoassay was performed using a universal microtiter plate as an antibody immobilization platform (see "Biosensors and Bioelectronics", 85, 611-617, 2016). Necessary parameter values were substituted into the mathematic model to compare the calculated theoretical dose-response curve for $Ca^{2+}$ immunoassay with that obtained experimentally. As a result, the two dose-response curves were in good agreement with each other (correlation coefficient ($R^2$) ≥99%, FIG. 10). For the curve obtained experimentally, the concentration variation (CV) in the $Ca^{2+}$ concentration range of ≤5 mM was found to be ≤15.6%. Particularly, the two dose-response curves were found to include a clinically important $Ca^{2+}$ concentration range of 0.25-2.5 mM, indirectly demonstrating that the $Ca^{2+}$ immunoassay developed by the present inventors is performed based on sequential reactions, like in the mathematic model proposed above.

Example 2: Development of $Ca^{2+}$ Immunobiosensor

1) Preparation of Immuno-Chromatography Membrane Strip (Immunostrip)

A reaction strip consisting of four functionally different membrane pads was prepared. The membrane pads partially overlap in the lengthwise direction. The four membrane pads are a polyester pad for sample loading (sample addition pad; 4×17 mm), a glass fiber pad containing a solid-dried signal conjugate (conjugate supply pad; 4×10 mm), an NC pad for signal generation (signal generation pad; 4×25 mm), and a cellulose chromatography paper for aqueous solution absorption (sample absorption pad; 4×15 mm) from the bottom. The signal generation pad was prepared by dispensing and immobilizing the monoclonal antibody (2 mg/mL) specifically recognizing a conformational change of the calcium binding protein and goat anti-mouse antibody (0.1 mg/mL) on given locations of the NC membrane using a non-contact type micro-dispenser (Bio-Dot, XYZ 3000, USA) and drying the antibodies at 37° C. for 1 h. Finally, the pads (each 4 mm wide) were arrayed such that the pads in contact with each other partially overlapped and were fixed on a plastic film using a double-sided tape. The surface of the signal generation pad was covered with a laminating plastic film (3×23 mm) except for one side (~0.5 mm) through which the horizontal absorption pad was accommodated.

2) Conventional Immuno-Chromatographic Assay

Just before $Ca^{2+}$ immunoassay using the immunostrip, a sample was mixed with a conjugate of the calcium binding protein and colloidal gold (diameter ~41.1 nm; see C of FIG. 11) and the mixture was added to the sample addition pad (see A of FIG. 11). The signal value from the specific antibody site (analyte site) immobilized on the signal generation pad was found to increase with the passage of time in the presence of calcium in the sample (e.g., 5 nM; see B of FIG. 11) (FIG. 8, D). In the case of a general chromatographic assay using colloidal gold as a signal substance, the signal value reached a steady state within 10-15 min from the start of the assay. For $Ca^{2+}$ analysis, the signal increased steadily by a non-specific influence of $Ca^{2+}$ on the gold signal substance.

This is predicted because calcium cations are ionically bonded to anions distributed on the surface of the gold particles, the calcium binding protein conjugated with the gold by physical adsorption is peeled off, the exposed gold surface non-specifically interacts with the membrane surface. To demonstrate this prediction, an immunostrip for a protein analyte was prepared by the same process. An increase in the concentration of $Ca^{2+}$ in the sample at a constant analyte concentration was found to lead to an increase in signal intensity (see A of FIG. 12). This problem can be solved by the use of covalent bonding upon conjugation of the protein with colloidal gold for $Ca^{2+}$ assay. As another solution to the problem, the present inventors designed a new 2-dimensional immuno-chromatographic assay using the gold conjugate (see B of FIG. 12).

3) 2-Dimensional Immuno-Chromatographic Assay

The 2-dimensional immuno-chromatographic assay was used to solve the problems encountered in the use of a colloidal gold conjugate prepared by the conventional method for calcium concentration measurement. For this purpose, the calcium binding protein was conjugated with biotin (b-CBP). A colloidal gold-streptavidin conjugate (SA-Gold) was prepared and used as a new constituent of an immunoassay kit. A vertical flow of the biotin-calcium binding protein conjugate was primarily reacted with a sample (100 μL) for 10 min and a horizontal flow of the streptavidin-gold conjugate was secondarily reacted with the sample (100 μL) for 5 min.

4) Signal Measurement Using Smartphone Detector

A smartphone-based detector was used to measure the signal generated in the signal generation pad of the reaction strip (see A of FIG. 13; "Biosensors and Bioelectronics", 85, 611-617, 2016). An illumination system was mounted in the detector (see B of FIG. 13) and the color signal generated on the reaction strip was captured with a camera mounted in the smartphone. The obtained signal image was digitized into an optical density using a home-made smartphone application (see C of FIG. 13). The digital values were transmitted to a personal computer where the integrated area of the peak was calculated using the Excel program to determine the signal value of the sensor for the concentration of $Ca^{2+}$ in the sample.

Example 3: Measurement of Dose Response and Confirmation of Analytical Performance of the Immunobiosensor 1) Dose Response and Correlation with Reference System In accordance with the 2-dimensional chromatographic assay, a biosensor was fabricated, the response of the sensor to the concentration of $Ca^{2+}$ in a standard serum sample was measured, and the measurement sensitivity was determined from the measured response (FIG. 14). When colloidal gold was used as a signal substance, the measurement sensitivity to $Ca^{2+}$ concentration and the concentration variation (CV) were found to be ~0.2 mM and ≤12.8%, respectively, from the dose-response curve. After linearization by log-logit transformation, the linearity of the dose-response curve corresponded to a correlation coefficient ($R^2$) of ≥98% (see A of FIG. 14). The performance of the developed immunobiosensor based on the $Ca^{2+}$ quantification method was compared with that of a commercial sensor (I-STAT, Abbott). A standard sample was prepared by adding $Ca^{2+}$ to actual serum, the analytical performances of the two sensors for the sample were measured simultaneously, and their measurement correlations were compared. As a result, the two analytical systems showed a correlation of ≥99% when human serum was used and a correlation of ≥98% when goat serum was used (see B of FIG. 14).

2) Interference by Cross-Reactivity

Samples containing eight cations (besides calcium) present in human serum and foods such as raw cow milk were prepared. The cross-reactivities with the calcium binding protein for other ions in the samples were measured using the developed analytical system (see FIG. 15). The concentrations of the cations were adjusted to 5-1,000 times higher concentrations than the normal concentrations of the cations in clinical samples. For 4 cations (P, Mg, K, and Al ions), the signals of the analytical system were not significantly higher than the background noise in all selected concentration ranges. In contrast, for the other four cations (Zn, Fe, Mn, and Al ions), high signals were observed at concentrations of 5 mM. No interference was found, which is explained by the fact that the cross-reactive cations are usually present at concentrations lower than ~30 µM in human serum. Tests were conducted on Zn and Fe ions. As a result, the cross-reactivities with the calcium binding protein were negligibly small at concentrations of ≤1 mM (see A of FIG. 16) and no interference was found when the samples were measured using the $Ca^{2+}$ immunobiosensor (see B of FIG. 16).

Although the measurement results were obtained only for $Ca^{2+}$ as a representative analyte of polyvalent metal ions, those skilled in the art can appropriately modify the system for the measurement of other metal ions ($Ca^{2+}$, $Fe^{2+}$, $Fe^{3+}$, $Zn^{2+}$, $Mn^{2+}$, $Mg^{2+}$, $Cu^{2+}$, etc.)

Hereinabove, the specific embodiments of the present invention have been explained in detail but the present invention is not limited thereto. It will be apparent to those skilled in the art that modifications and improvements can be made without departing from the spirit and scope of the invention. Simple modifications and alterations of the present invention belong to the scope of the present invention, and the specific scope of the present invention will be clearly defined by the appended claims.

What is claimed is:

1. An immunobiosensor based on a membrane lateral flow immuno-chromatographic assay (LF-ICA), comprising: a metal binding protein whose conformation changes upon reaction with a metal ion in a sample; a sensing antibody reacting with the conformationally changed metal binding protein as an antigen; a signal substance conjugated with the metal binding protein to form a signal conjugate; a signal generator reacting with the signal conjugate to generate a reaction signal; a reaction strip in the form of a porous membrane adapted to move the sample and where the antigen-antibody reaction occurs and the reaction signal is generated; a signal generator supply pad supplying the signal generator to the reaction strip; and a signal generator absorption pad absorbing the signal generator, wherein the reaction strip comprises a sample addition pad absorbing the sample and a signal generation pad connected to the sample addition pad in the lengthwise direction and immobilized with the sensing antibody to generate the reaction signal, wherein one of the signal generator supply pad and the signal generator absorption pad is arranged at one lateral side of the signal generation pad and the other one is arranged at the other lateral side of the signal generation pad, and wherein the signal generator is introduced into the signal generator supply pad, transferred in the widthwise direction of the signal generation pad, and absorbed into the signal generator absorption pad.

2. The immunobiosensor according to claim 1, further comprising a conjugate supply pad connecting the sample addition pad to the signal generation pad and supplying the signal conjugate to the signal generation pad.

3. The immunobiosensor according to claim 2, wherein the reaction strip is constructed such that one end of the conjugate supply pad is arranged on one end of the signal generation pad and one end of the sample addition pad is arranged on the other end of the conjugate supply pad, and the immunobiosensor further comprises a sample absorption pad arranged on the other end of the signal generation pad to absorb the sample having passed through the signal generation pad.

4. The immunobiosensor according to claim 2, wherein the signal conjugate is dried into a solid and is arranged on the conjugate supply pad.

5. The immunobiosensor according to claim 1, wherein a solution of the metal binding protein is absorbed into the sample addition pad or is arranged in the sample addition pad and is dissolved by the sample.

6. The immunobiosensor according to claim 1, wherein the reaction signal is a fluorescence, color, luminescence, electrochemical, thermal or magnetic signal.

7. The immunobiosensor according to claim 1, wherein the metal ion comprises at least one metal ion selected from the group consisting of $Ca^{2+}$, $Fe^{2+}$, $Fe^{3+}$, $Zn^{2+}$, $Mn^{2+}$, $Mg^{2+}$, and $Cu^{2+}$.

8. The immunobiosensor according to claim 1, wherein the metal ion is a calcium ion, the metal binding protein is a calcium binding protein, the signal substance is biotin, the signal generator is colloidal gold conjugated with streptavidin, and the reaction signal is a color signal generated from the linking rings between the biotin and the streptavidin.

9. The immunobiosensor according to claim 8, wherein the calcium binding protein comprises at least one protein selected from the group consisting of glucose-galactose binding proteins, calmodulin, calcium binding enzymes, and genetically substituted proteins.

10. The immunobiosensor according to claim 1, wherein the sensing antibody comprises at least one antibody selected from the group consisting of monoclonal antibodies, polyclonal antibodies, phage display antibodies, and gene recombinant antibodies.

11. The immunobiosensor according to claim 1, further comprising an accommodation space in which the reaction strip is arranged and a cartridge comprising a sample inlet through which the sample is introduced into the sample addition pad and a detection window through which signal generation pad is exposed.

12. A sensor system comprising: the immunobiosensor according to claim 1; a smart device comprising a camera capable of capturing a color signal as the reaction signal generated in the signal generation pad of the immunobiosensor as an image; and a holder having a slot into which the immunobiosensor is inserted and adapted to hold the smart device.

13. The sensor system according to claim 12, further comprising a light source arranged in the smart device holder to emit light.

14. The sensor system according to claim 12, wherein the captured color signal is converted into digital data by an application on the smart device.

* * * * *